(12) United States Patent
Stone et al.

(10) Patent No.: US 8,147,546 B2
(45) Date of Patent: Apr. 3, 2012

(54) METHOD AND APPARATUS FOR GRAFT FIXATION

(75) Inventors: Kevin T Stone, Winona Lake, IN (US); Jason D Meridew, Syracuse, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 591 days.

(21) Appl. No.: 11/717,792

(22) Filed: Mar. 13, 2007

(65) Prior Publication Data
US 2008/0228271 A1 Sep. 18, 2008

(51) Int. Cl.
*A61F 2/08* (2006.01)
(52) U.S. Cl. ............... 623/13.14; 623/13.11; 623/13.17
(58) Field of Classification Search ............ 623/13.11, 623/13.12, 13.14, 13.15, 13.13, 13.17
See application file for complete search history.

(56) References Cited

U.S. PATENT DOCUMENTS

| | | | |
|---|---|---|---|
| 0,461,621 A | 10/1891 | Rogers | |
| 1,762,394 A | 6/1930 | Hosking | |
| 1,940,878 A | 12/1933 | Olson | |
| 2,640,521 A | 6/1953 | Zavoico | |
| 2,695,607 A | 11/1954 | Hipps et al. | |
| 3,832,931 A | 9/1974 | Talan | |
| 3,871,379 A | 3/1975 | Clarke | |
| 4,044,647 A | 8/1977 | Takahashi et al. | |
| 4,053,982 A | 10/1977 | Weissman | |
| D249,705 S | 9/1978 | London | |
| 4,257,411 A | 3/1981 | Cho | |
| 4,338,054 A | 7/1982 | Dahl | |
| 4,386,179 A * | 5/1983 | Sterling | 524/269 |
| 4,535,768 A | 8/1985 | Hourahane et al. | |
| 4,537,185 A | 8/1985 | Stednitz | |
| 4,756,307 A | 7/1988 | Crowninshield | |
| 4,903,692 A | 2/1990 | Reese | |
| 4,922,897 A | 5/1990 | Sapega et al. | |
| 4,932,972 A * | 6/1990 | Dunn et al. | 623/13.19 |
| 4,950,270 A | 8/1990 | Bowman et al. | |
| 4,985,032 A | 1/1991 | Goble | |
| 4,998,937 A | 3/1991 | Grimes | |
| 5,004,474 A | 4/1991 | Fronk et al. | |
| 5,019,078 A | 5/1991 | Perren et al. | |
| 5,026,374 A | 6/1991 | Dezza et al. | |

(Continued)

FOREIGN PATENT DOCUMENTS

| | | |
|---|---|---|
| EP | 1360949 | 11/2003 |
| FR | 2684543 | 6/1993 |

OTHER PUBLICATIONS

Allen et al. "Degradation and stabilisation of styrene±ethylene±butadiene±styrene (SEBS) block copolymer." Polymer Degradation and Stability. V 71, p. 113-122. 2001.*

* cited by examiner

*Primary Examiner* — David H Willse
*Assistant Examiner* — Tiffany Shipmon
(74) *Attorney, Agent, or Firm* — Harness, Dickey (57) ABSTRACT

A method and apparatus for surgically coupling a soft tissue replacement into a tunnel of a bone are disclosed. The method includes forming a loop of a soft tissue or soft tissue replacement. A pair of prosthetics are coupled to the loop of soft tissue to form an artificial bone-tendon-bone graft. The prosthetics and soft tissue are then placed within a tunnel formed in a bone. The relative position of the prosthetic is then fixed with respect to the tunnel.

14 Claims, 5 Drawing Sheets

U.S. PATENT DOCUMENTS

| | | | |
|---|---|---|---|
| 5,030,219 A | 7/1991 | Matsen, III et al. | |
| 5,041,129 A | 8/1991 | Hayhurst et al. | |
| 5,098,435 A | 3/1992 | Stednitz et al. | |
| 5,100,405 A | 3/1992 | McLaren | |
| 5,100,417 A | 3/1992 | Cerier et al. | |
| 5,108,396 A | 4/1992 | Lackey et al. | |
| 5,112,336 A | 5/1992 | Krevolin et al. | |
| 5,129,902 A | 7/1992 | Goble et al. | |
| 5,139,520 A | 8/1992 | Rosenberg | |
| 5,141,520 A | 8/1992 | Goble et al. | |
| 5,176,682 A | 1/1993 | Chow | |
| 5,192,322 A | 3/1993 | Koch et al. | |
| 5,201,744 A | 4/1993 | Jones | |
| 5,224,946 A | 7/1993 | Hayhurst et al. | |
| 5,234,434 A | 8/1993 | Goble et al. | |
| 5,234,444 A | 8/1993 | Christoudias | |
| 5,257,996 A | 11/1993 | McGuire | |
| 5,258,016 A | 11/1993 | DiPoto et al. | |
| 5,266,075 A | 11/1993 | Clark et al. | |
| 5,300,077 A | 4/1994 | Howell | |
| 5,350,380 A | 9/1994 | Goble et al. | |
| 5,354,298 A | 10/1994 | Lee et al. | |
| 5,354,300 A | 10/1994 | Goble et al. | |
| 5,356,413 A | 10/1994 | Martins et al. | |
| 5,370,646 A | 12/1994 | Reese et al. | |
| 5,370,662 A | 12/1994 | Stone et al. | |
| 5,391,029 A | 2/1995 | Fardell | |
| 5,393,302 A | 2/1995 | Clark et al. | |
| 5,397,356 A | 3/1995 | Goble et al. | |
| D357,534 S | 4/1995 | Hayes | |
| 5,423,823 A | 6/1995 | Schmieding | |
| 5,425,733 A | 6/1995 | Schmieding | |
| 5,431,651 A | 7/1995 | Goble | |
| 5,437,677 A | 8/1995 | Shearer et al. | |
| 5,454,365 A | 10/1995 | Bonutti | |
| 5,456,722 A | 10/1995 | McLeod et al. | |
| 5,480,403 A | 1/1996 | Lee et al. | |
| 5,507,812 A | 4/1996 | Moore | |
| 5,540,703 A | 7/1996 | Barker, Jr. et al. | |
| 5,545,180 A | 8/1996 | Le et al. | |
| 5,549,676 A | 8/1996 | Johnson | |
| 5,562,671 A | 10/1996 | Goble et al. | |
| 5,593,408 A | 1/1997 | Gayet et al. | |
| 5,601,562 A | 2/1997 | Wolf et al. | |
| 5,618,314 A | 4/1997 | Harwin et al. | |
| 5,632,748 A | 5/1997 | Beck, Jr. et al. | |
| 5,643,273 A | 7/1997 | Clark | |
| 5,643,320 A | 7/1997 | Lower et al. | |
| 5,665,121 A | 9/1997 | Gie et al. | |
| 5,674,224 A | 10/1997 | Howell et al. | |
| 5,800,544 A * | 9/1998 | Demopulos et al. | 623/13.13 |
| 5,849,013 A | 12/1998 | Whittaker et al. | |
| 5,868,789 A | 2/1999 | Huebner | |
| 5,891,150 A | 4/1999 | Chan | |
| 5,895,425 A | 4/1999 | Grafton et al. | |
| 5,918,604 A | 7/1999 | Whelan | |
| 5,931,839 A | 8/1999 | Medoff | |
| 5,931,869 A | 8/1999 | Boucher et al. | |
| 5,941,885 A | 8/1999 | Jackson | |
| 5,964,764 A | 10/1999 | West, Jr. et al. | |
| 5,980,558 A | 11/1999 | Wiley | |
| 5,984,966 A | 11/1999 | Kiema et al. | |
| 6,039,739 A | 3/2000 | Simon | |
| 6,066,173 A | 5/2000 | McKernan et al. | |
| 6,068,648 A | 5/2000 | Cole et al. | |
| 6,110,211 A | 8/2000 | Weiss | |
| 6,113,604 A | 9/2000 | Whittaker et al. | |
| 6,132,433 A | 10/2000 | Whelan | |
| 6,146,406 A | 11/2000 | Shluzas et al. | |
| 6,187,742 B1 | 2/2001 | Wozney et al. | |
| 6,224,598 B1 | 5/2001 | Jackson | |
| 6,231,608 B1 | 5/2001 | Stone | |
| 6,231,611 B1 | 5/2001 | Mosseri et al. | |
| 6,267,766 B1 | 7/2001 | Burkhart | |
| 6,280,472 B1 | 8/2001 | Boucher et al. | |
| 6,280,474 B1 | 8/2001 | Cassidy et al. | |
| 6,306,138 B1 | 10/2001 | Clark et al. | |
| 6,325,804 B1 | 12/2001 | Wenstrom, Jr. et al. | |
| 6,342,056 B1 | 1/2002 | Mac-Thiong et al. | |
| 6,371,124 B1 | 4/2002 | Whelan | |
| 6,375,684 B1 | 4/2002 | Kriek et al. | |
| 6,379,384 B1 | 4/2002 | McKernan et al. | |
| 6,383,199 B2 | 5/2002 | Carter et al. | |
| 6,436,099 B1 | 8/2002 | Drewry et al. | |
| 6,440,373 B1 | 8/2002 | Gomes et al. | |
| 6,454,768 B1 | 9/2002 | Jackson | |
| 6,494,913 B1 | 12/2002 | Huebner | |
| 6,497,726 B1 | 12/2002 | Carter et al. | |
| 6,499,486 B1 | 12/2002 | Chervitz et al. | |
| 6,511,958 B1 | 1/2003 | Atkinson et al. | |
| 6,514,514 B1 | 2/2003 | Atkinson et al. | |
| 6,517,546 B2 | 2/2003 | Whittaker et al. | |
| 6,517,579 B1 | 2/2003 | Paulos et al. | |
| 6,524,328 B2 | 2/2003 | Levinson | |
| 6,537,319 B2 | 3/2003 | Whelan | |
| 6,540,783 B1 | 4/2003 | Whittaker et al. | |
| 6,562,043 B1 | 5/2003 | Chan | |
| 6,562,044 B1 * | 5/2003 | Cooper | 606/300 |
| 6,562,071 B2 | 5/2003 | Jarvinen | |
| 6,589,281 B2 | 7/2003 | Hyde, Jr. | |
| 6,610,064 B1 | 8/2003 | Goble et al. | |
| 6,623,524 B2 | 9/2003 | Schmieding | |
| 6,673,115 B2 | 1/2004 | Resch et al. | |
| 6,712,823 B2 | 3/2004 | Grusin et al. | |
| 6,730,089 B2 | 5/2004 | Jackson | |
| 6,733,529 B2 | 5/2004 | Whelan | |
| 6,752,830 B1 | 6/2004 | Goble et al. | |
| 6,755,840 B2 | 6/2004 | Boucher et al. | |
| 6,780,188 B2 | 8/2004 | Clark et al. | |
| 6,878,166 B2 | 4/2005 | Clark et al. | |
| 6,887,271 B2 * | 5/2005 | Justin et al. | 623/13.14 |
| 7,022,124 B2 | 4/2006 | Takei et al. | |
| 7,033,364 B1 | 4/2006 | Walters et al. | |
| 7,229,448 B2 | 6/2007 | Goble et al. | |
| 7,285,121 B2 | 10/2007 | Braun et al. | |
| 7,309,337 B2 | 12/2007 | Colleran et al. | |
| 7,341,592 B1 | 3/2008 | Walters et al. | |
| 7,458,975 B2 | 12/2008 | May et al. | |
| 7,588,595 B2 | 9/2009 | Miller et al. | |
| 7,601,165 B2 | 10/2009 | Stone | |
| 7,645,293 B2 | 1/2010 | Martinek et al. | |
| 2001/0039455 A1 | 11/2001 | Simon et al. | |
| 2001/0044627 A1 | 11/2001 | Justin | |
| 2001/0047210 A1 | 11/2001 | Wolf | |
| 2001/0053934 A1 | 12/2001 | Schmieding | |
| 2002/0019635 A1 | 2/2002 | Wenstrom et al. | |
| 2002/0058941 A1 | 5/2002 | Clark et al. | |
| 2002/0077631 A1 * | 6/2002 | Lubbers et al. | 606/72 |
| 2002/0087160 A1 | 7/2002 | Clark et al. | |
| 2002/0099381 A1 | 7/2002 | Maroney | |
| 2002/0111689 A1 | 8/2002 | Hyde | |
| 2002/0111690 A1 | 8/2002 | Hyde | |
| 2002/0133153 A1 | 9/2002 | Hyde | |
| 2002/0138148 A1 | 9/2002 | Hyde | |
| 2002/0138149 A1 | 9/2002 | Hyde | |
| 2003/0028194 A1 | 2/2003 | St. Pierre et al. | |
| 2003/0032961 A1 | 2/2003 | Pelo et al. | |
| 2003/0065332 A1 | 4/2003 | TenHuisen et al. | |
| 2003/0097179 A1 | 5/2003 | Carter et al. | |
| 2003/0105524 A1 | 6/2003 | Paulos et al. | |
| 2003/0130735 A1 * | 7/2003 | Rogalski | 623/13.15 |
| 2003/0163202 A1 | 8/2003 | Lakin | |
| 2004/0087953 A1 | 5/2004 | Singhatat et al. | |
| 2004/0092936 A1 | 5/2004 | Miller et al. | |
| 2005/0038426 A1 * | 2/2005 | Chan | 606/60 |
| 2005/0137704 A1 * | 6/2005 | Steenlage | 623/13.14 |
| 2005/0149187 A1 | 7/2005 | Clark et al. | |
| 2005/0177165 A1 | 8/2005 | Zang et al. | |
| 2005/0197662 A1 | 9/2005 | Clark et al. | |
| 2005/0203622 A1 * | 9/2005 | Steiner et al. | 623/13.14 |
| 2005/0273003 A1 | 12/2005 | Walters et al. | |
| 2006/0229722 A1 * | 10/2006 | Bianchi et al. | 623/13.14 |
| 2007/0162123 A1 | 7/2007 | Whittaker et al. | |
| 2007/0168043 A1 | 7/2007 | Ferree | |
| 2008/0027443 A1 | 1/2008 | Lambert | |

METHOD AND APPARATUS FOR GRAFT FIXATION

FIELD

The present disclosure relates to endoscopic soft tissue replacement fixation. More particularly, the present disclosure relates to an apparatus and a method to reconstruct an anterior cruciate ligament with soft tissue replacements within a femoral or tibial tunnel.

BACKGROUND

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

It has been difficult to insert and fasten a soft tissue replacement in a blind hole or tunnel. Attempts have been made to thread the soft tissue replacement through the tunnel and over an anchor, but with some difficulty. As such, improvements which provide a quick and efficient way to couple a soft tissue replacement to an implanted anchoring system are desirable.

Currently, fascia lata soft tissue replacements are flexible strands which are affixed to a threaded stud and turned into the femoral tunnel. Unfortunately, this procedure may result in the soft tissue replacement being wrapped upon itself during insertion. Hamstring soft tissue replacements are also currently fixed over a screw in the tibial tunnel and fixed on the lateral femur. This technique may require the femoral tunnel to completely penetrate the femur. In addition, according to present procedures, fixation of the soft tissue replacement on the femoral side may require a large incision.

Additional procedures include the use of bone-tendon-bone grafts which have been pre or intra-operatively harvested from a donor site. In addition to the problems associated with graft retrieval, these bone-tendon-bone grafts are of fixed length. This fixed length significantly reduces their usability, as it is not possible to easily adjust the tension or length of the implanted tendon.

While offering certain improvements in arthroscopic surgery to repair ligaments, the prior art may still be improved upon to overcome the limitations on the endoscopic hamstring soft tissue replacement fixation due, in many instances, to the weakness of the mechanism used to couple the tendon soft tissue replacement to an aperture formed within a bone. Other techniques attempt to use biological fixation to augment or replace mechanical fixation. While increasing fixation strength, these techniques require time to fully realize their fixation potential. Additionally the techniques may take additional surgical time and resources that a purely mechanical fixation technique may not require.

SUMMARY

A method and apparatus are taught herein which function to couple a soft tissue replacement material to a bone structure. The apparatus includes a pair of members that are integrally coupled to a loop of soft tissue replacement material to form an artificial bone-tendon-bone graft. The members, which are formed around or frictionally coupled to the soft tissue replacement material, are used to lock the soft tissue replacement material into a pair of apertures formed in a bone.

In one embodiment, a method for surgically coupling a soft tissue replacement into a tunnel of a bone is disclosed. The method includes forming a loop of a soft tissue or soft tissue replacement by folding the grafts so as to position the ends together. A prosthetic is coupled to the loop of soft tissue utilizing casting techniques. The prosthetic and soft tissue are placed within a tunnel formed in a bone. The relative position of the prosthetic is then fixed with respect to the tunnel.

In another embodiment, a method of surgically coupling a soft tissue implant to a bone is disclosed. The method includes coupling a soft tissue replacement to a prosthetic formed of a pair of interlocking members to form a prosthetic assembly. A suture is then coupled to the prosthetic assembly. The suture is passed through the bore to position the prosthetic within the bone. The relative position of the prosthetic is then fixed with respect to the bone.

In another embodiment, a method of coupling a soft tissue replacement to a bone is disclosed. The method includes frictionally engaging a pair of prosthetics with a loop of soft tissue replacement material to form an artificial bone-tendon-bone prosthetic assembly. A suture, which is coupled to the prosthetic assembly, is passed through an aperture in the bone to position the prosthetic assembly within the aperture, and apply tension to the soft tissue replacement.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

The descriptions of the teachings are merely exemplary in nature and, thus, variations that do not depart from the gist of the teachings are intended to be within the scope of the invention. Such variations are not to be regarded as a departure from the spirit and scope of the teachings.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
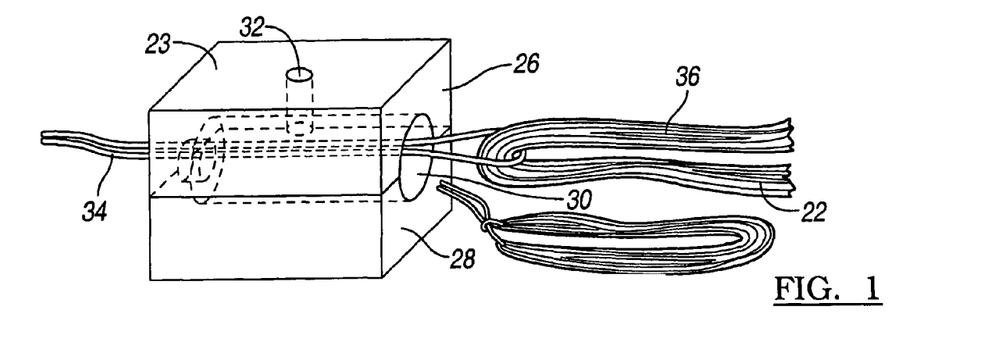
FIGS. 1 and 2 represent a method of forming a prosthetic about a graft according to one embodiment of the teachings herein.
Figure 2:
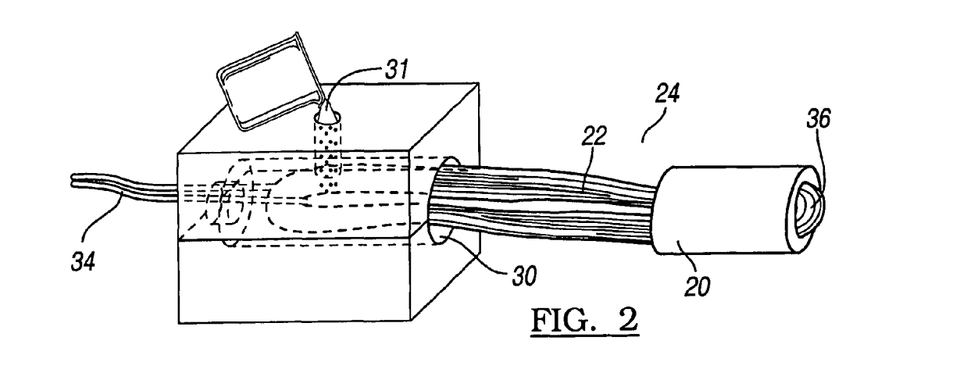

FIGS. 1 and 2 represent a system and method of forming a prosthetic 20 about a graft or graft replacement material 22 to form an artificial bone-tendon or bone-tendon-bone prosthetic assembly 24 according to one embodiment disclosed herein. Shown is a mold 23 having a first and second dies 26 and 28, which define a cavity 30 therethrough. Defined by the first die 26 is an injection port 32, which allows for the filling of the through cavity 30 with biocompatible material. As shown in FIG. 1, a suture 34 is threaded through a loop 36 of the replacement graft material 22, or tied to the ends of the graft material 22.

The suture 34 and loop 36 of graft material 22 are pulled through the through cavity 30 to position the loop 36 of graft 22 in the cavity 30. After the loop 36 of graft material 22 is placed within the through cavity 30, an uncured biocompatible polymer material 31, bone cement, or a calcium phosphate containing mixture is then injected through injection port 32. After the curing or setting of the polymer 31, the first and second dies 26 and 28 are separated exposing the prosthetic 20 intimately frictionally and/or mechanically coupled to the graft 22. In this regard, the exterior surface of a portion of the replacement graft is completely enclosed or encapsulated by the prosthetic 20. In other words, the prosthetic can function to protect this portion of the graft replacement 22 from interaction with hardware used to couple the graft assembly 24 to the bone. The replacement graft 22 may be a preoperative or intraoperatively harvested tendon such has a hamstring or may be xenograft, allograft, or artificial graft material.

Figure 3A:
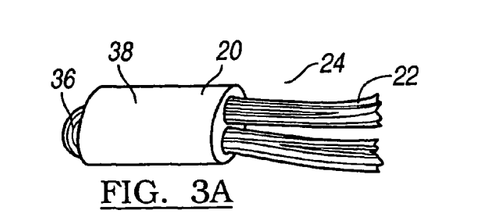
FIGS. 3a-3c represent prosthetics formed using the method shown in FIGS. 1 and 2.
Figure 3B:
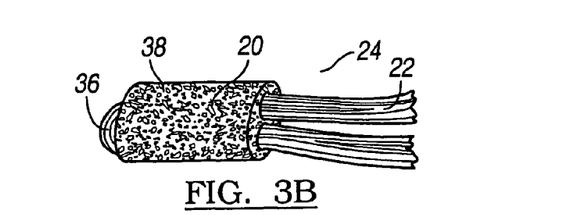
Figure 3C:
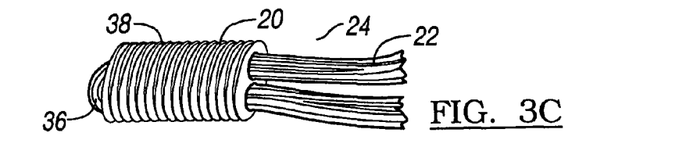

As shown in FIGS. 3a-3c, the exterior surface 38 of the prosthetic 20 can be textured by modifying the interior surface of the cavity 30. In this regard, the exterior surface 38 can be smooth, porous, or define an external thread. As described below, the exterior surface 38 can also define locking features which interface with a fastener or an interior surface of an implant accepting bore to fix the prosthetic assembly 24 within an aperture. Additionally, the exterior surface 38 can be shaped or machined after molding.

Figure 4:
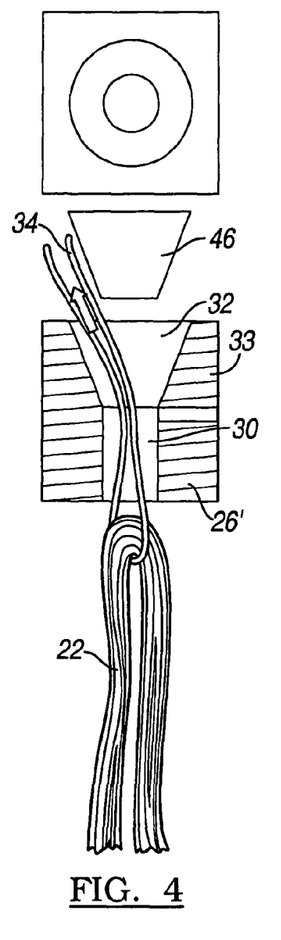
FIG. 4 represents an alternate mold used to form the prosthetics shown in FIGS. 3a-3c.
Figure 6A:
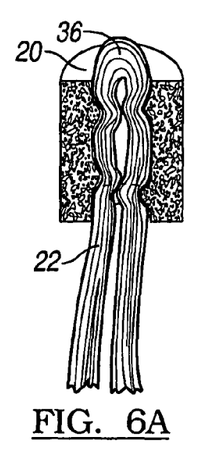
FIGS. 6a-6c represent prosthetics utilizing the tying mechanisms shown in FIGS. 5a-5d.

FIG. 4 represents an alternate mold 33 for forming the prosthetics shown in FIGS. 3a-3c. As shown, the cavity 30 can be defined by a single die 26'. This die 26' defines a generally cylindrical cavity 30, which has a conical injection port 32. The suture 34 can be threaded through the injection port 32, pulling the soft tissue replacement within the cavity 30. After the biocompatible material is placed into the conical injection port 32, a plunger-type cap 46 can be inserted into the conical injection port 32 to press the biocompatible material into the cylindrical cavity. It is envisioned that the injection port 32 can be threaded or configured to be formed to accept a syringe, which can be used to inject biological material or bone cement. The cavity 30 can be tapered to facilitate removal of the prosthetic assembly 24 after setting of the polymer 31. Alternately, the interior surface of the molds 26 can have a plurality of members (not shown) which function to position the graft material 22 centrally within the mold 26. Further, these members can compress the graft material 22 at discrete locations to allow the formation of a plug with interdigitation of cement. (see FIG. 6a).

Figure 5A:
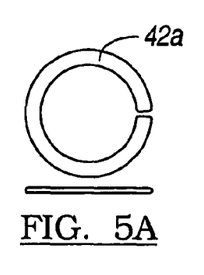
FIGS. 5a-5d represent optional tying mechanisms.
Figure 5B:
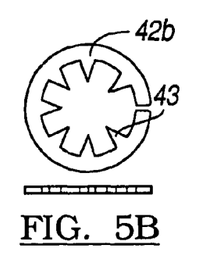
Figure 5C:
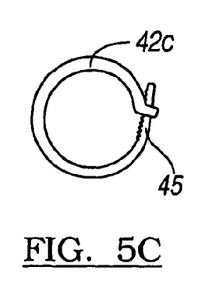
Figure 5D:
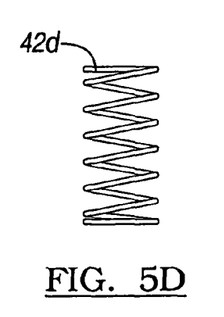
Figure 6B:
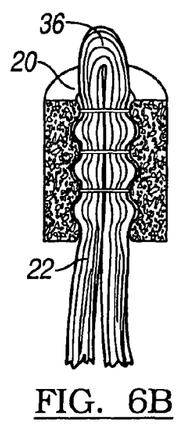

FIGS. 5a-5d represent optional tying mechanisms 42a-42d, which are used to bind the loop 36 of graft material 22. As shown in FIG. 6b, a plurality of tying mechanisms 42a-42d can be annularly disposed about the loop 36 of the graft material 22. The interior surface of the tying mechanisms 42a-42d can be textured 43 so as to prevent the relative displacement of the tying mechanism 42a-42d with respect to the loop 36 of the graft material 22. As shown in FIG. 5c, the tying mechanism 42a-42d can have structures 45 that allow for the non-releasable or releasable tightening of the tying mechanism about the graft loop 36.

Figure 6C:
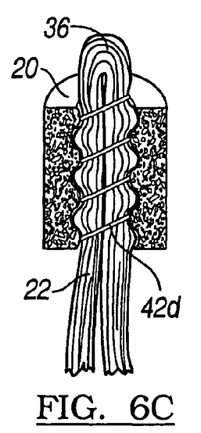

As shown in FIG. 6c, a single tying member 42d can be formed as a coil spring 42d. The coil spring 42d can be radially expanded so as to allow for the insertion of the loop 36 into an inner space defined by the coils of the coil spring 42d. After the tying mechanism is coupled to the graft loop 36, the subassembly is positioned within the mold as disclosed above to form the prosthetic assembly 24. Depicted is a cross-sectional view of the graft loop 36 disposed within the formed prosthetic 20. Shown is the tying mechanism 42d disposed about the graft loop 36 which is fully disposed within the prosthetic 20. While a distal end of the loop 36 of graft material is shown being exposed to allow acceptance of a suture, it is equally envisioned the distal end of the loop 36 can be fully incorporated into the prosthetic 20.

Figure 7A:
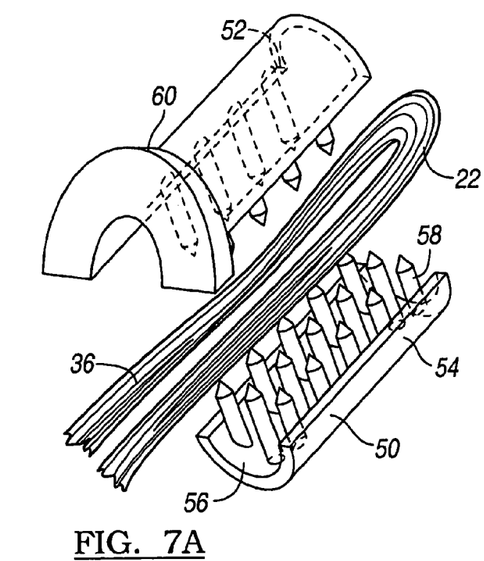
FIGS. 7a and 7b represent coupling an alternate prosthetic to a graft and to the insertion thereof.

FIG. 7a represents an alternate prosthetic 50 configured to be coupled to the loop 36 of the graft material 22. The prosthetic 50, as well as those described below, are formed of first and second members 52 and 54 which are mechanically, ultrasonically, or adhesively coupled together. The members 52 and 54 together define a graft accepting through passage 56. Disposed within the through passage 56 are a plurality of counter-posed graft engaging members 58. The counter-posed graft engaging members 58 are configured to pierce or frictionally engage the graft material 22. Additionally, optional coupling surfaces can be formed on the counter-posed graft engaging members 58 to couple the first and second members 52 and 54 together.

Figure 7B:
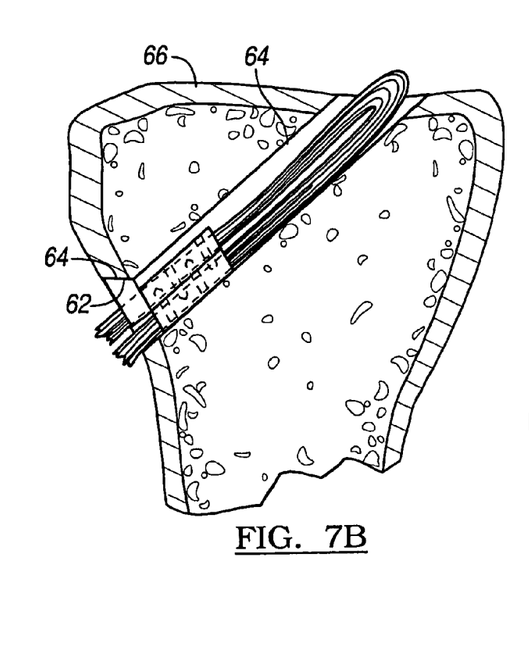

As described above, optionally disposed on an exterior surface of the prosthetic 50 is a bone engaging bearing surface 60. This bone engaging bearing surface 60 can be on either or both of the first and second members 52 and 54. FIG. 7b shows the prosthetic 50 disposed within a bore 64 defined in a tibia 66. As shown, the bone engaging bearing surface 60 has an angled bearing surface 62, which interfaces with a counter sunk surface 65 formed in an outer surface of the tibia 66. The prosthetic 50 is formed of a biocompatible material. In this regard, the material can be any biocompatible material such as metal or polymer such as ultrasonically bondable PEEK, PEKK, or can be a resorbable material such as Lactosorb.

Figure 8A:
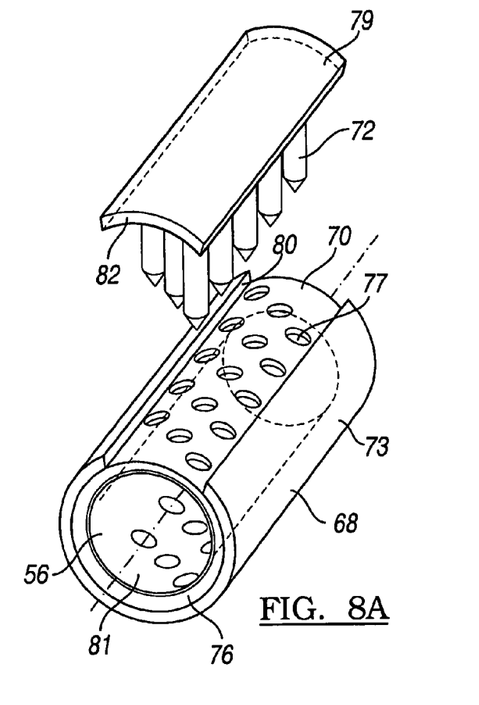
FIGS. 8a and 8b represent an alternate coupling prosthetic.
Figure 8B:
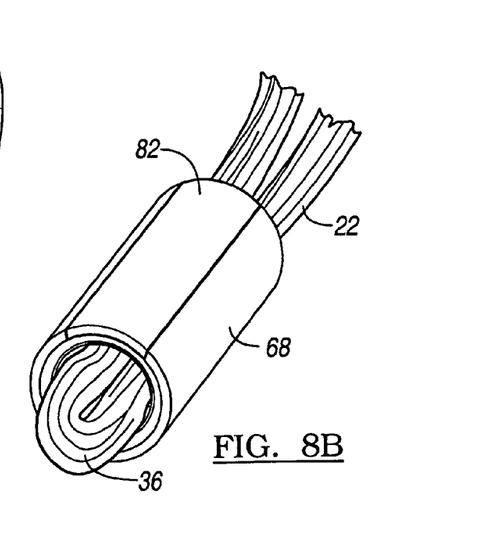

FIGS. 8a and 8b represent perspective views of an alternate prosthetic 68 according to the disclosure herein. The prosthetic 68 is formed of first and second members 70 and 72. The first member 70 is generally cylindrical having a graft loop accepting through passage 74. The first member 70 can be formed of an inner member 76 and an outer member 78. The inner member defines a plurality of graft engaging member accepting apertures 77. These apertures 77 can be formed on opposite sides of the first member 70 to facilitate the locking of the graft engaging member to the first member 70. The outer member 78 is annularly disposed about the inner member 76. In this regard, the outer member 78 defines a groove 80, which generally surrounds the graft engaging member apertures 76. The second member 79 is generally arcuate and is configured to be disposed within the groove 80 formed by the outer member 78. Disposed on a convex inner surface 82 of the second member 79 are a plurality of graft engaging members 72. These graft engaging members 72 are configured to be aligned with the graft engaging member apertures 77 formed in the first member 70.

As shown in FIG. 8b, the graft loop 36 is fed through the loop accepting aperture 81. The graft engaging members 72 are aligned with the apertures 77. The second member is displaced toward the first member, causing the graft engaging member 72 to pierce or frictionally engage the graft loop 36. The first and second members 70 and 72 are then ultrasonically, adhesively, press-fit or heat bonded together to form a single prosthetic.

As shown in FIGS. 9a-9d, the prosthetic 50 can have a plurality of coupling flanges 84, which can be disposed about a mating surface 86. These flanges 84 are configured to interface with corresponding slots 88 in the first member. As described above, the exterior surface 90 of the implant 50 can be textured. As shown, the exterior surface 90 can define an angled threaded depression 92, which is configured to accept a bone engaging screw 100 (see FIG. 10). Additionally the exterior surface can define a generally concave threaded depression 93 which runs the length of the length of the implant.

Figure 9A:
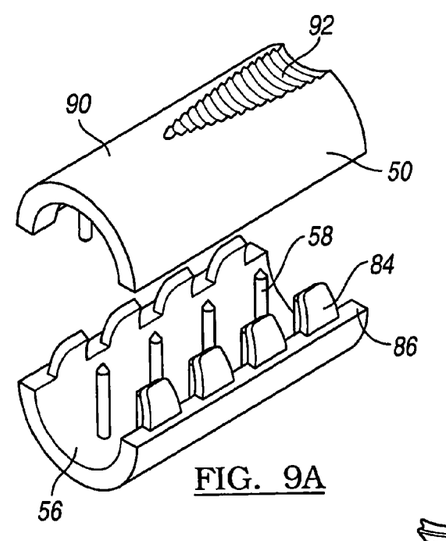
FIGS. 9a-9d represent perspective and side views of an alternate embodiment.
Figure 9B:
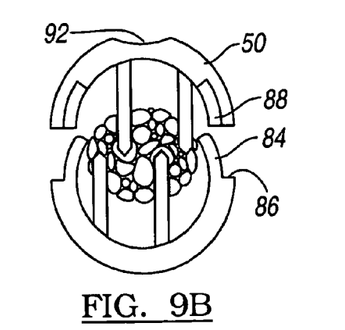
Figure 9C:
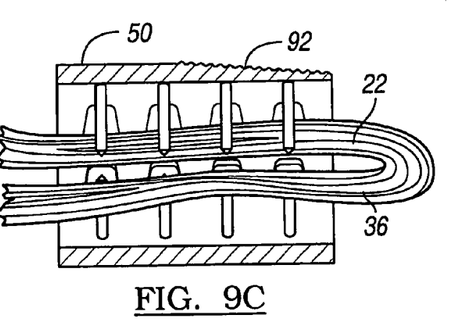
Figure 9D:
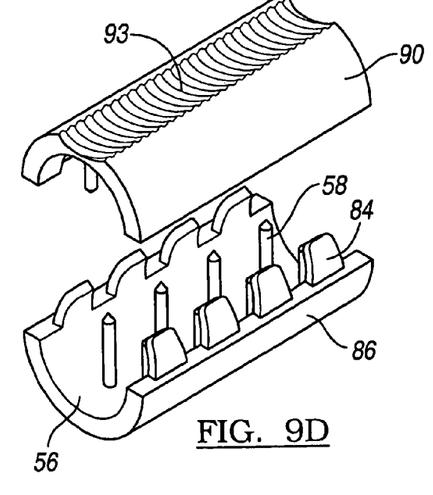
Figure 10:
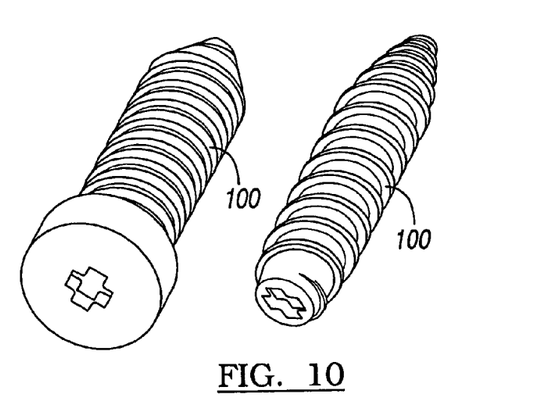
FIG. 10 represents fasteners used to couple the graft construction to a femoral tunnel.
Figure 11:
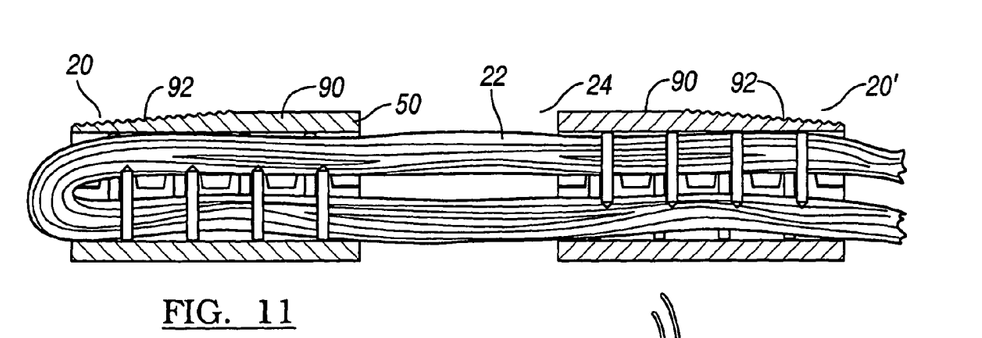
FIG. 11 represents an artificial bone-tendon-bone fastener graft construction.

FIG. 11 represents an artificial bone-tendon-bone prosthetic assembly 24. The assembly 24 includes a pair of prosthetics 20 as shown in FIG. 9d coupled to proximal and distal ends of a loop of graft material. It is envisioned that the prosthetics 20 used to form the artificial bone-tendon-bone prosthetic assembly 24 can utilize any of the aforementioned prosthetics 20. Additionally shown is the suture used to install the artificial bone-tendon-bone prosthetic assembly 24 into the bone.

Figure 12:
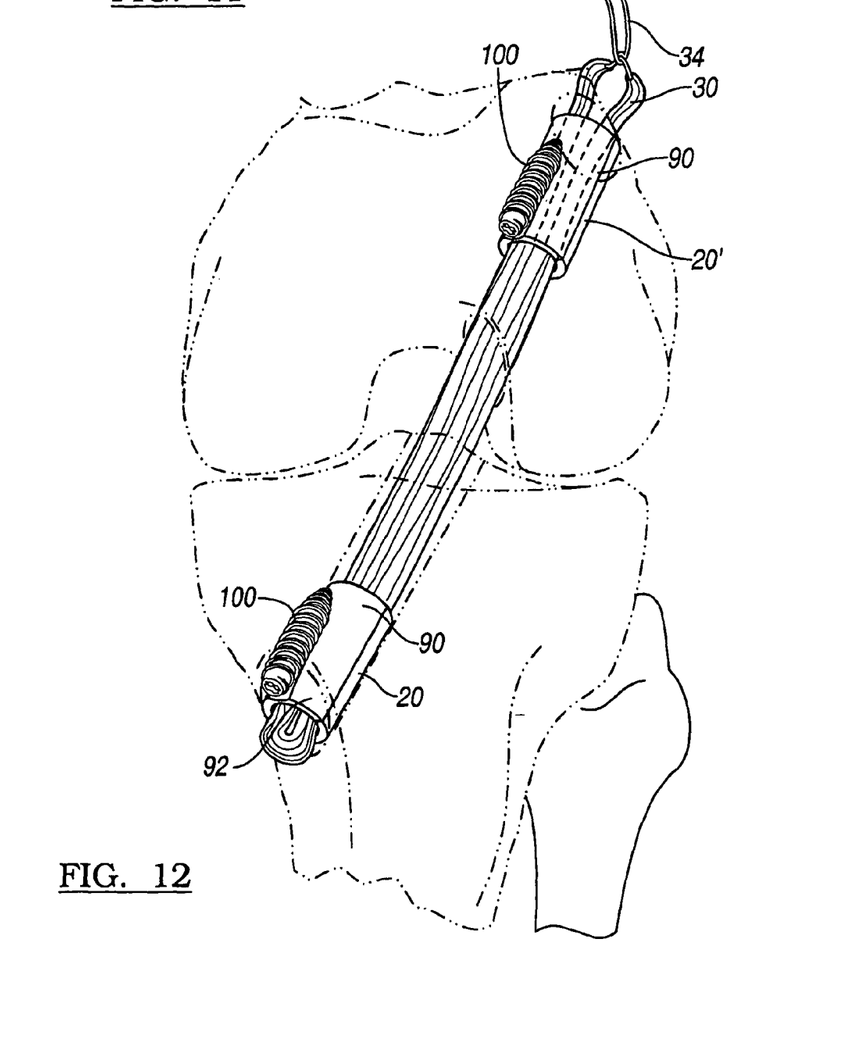
FIG. 12 represents the construction according to FIG. 9c coupled to a tibial and femoral tunnel using the fastener of FIG. 10.

FIG. 12 depicts an implant 50 coupled to a graft 22 disposed within a tibial and femoral tunnel. As mentioned above, the graft 22 is coupled to the prosthetic 20 to form an artificial bone-tendon or bone-tendon-bone prosthetic assembly 24. It is envisioned the physician can intraoperatively determine the desired graft or graft assembly length and appropriate graft tension. The first prosthetic 20 is coupled to a first end of the replacement graft either preoperatively or intraoperatively using any of the methods described above. The physician then determines an appropriate length for the graft material 22 by measuring an anatomical distance.

An appropriate amount of tension is applied to the graft and the length of the graft is then marked. A second prosthetic 20' is then coupled to the prosthetic assembly at the marked location. This location is a function of the measured anatomical distance, which takes into account mounting structures. This provides an appropriately sized artificial bone-tendon-bone prosthetic. It is envisioned the second prosthetic 20 would then be coupled to the graft material intraoperatively. Optionally, a kit of preformed artificial bone-tendon graft assemblies with an associated second prosthetic can be provided. Additionally, the kit can contain the molds 26 or 26' shown in FIG. 1 or 4, and a package of premeasured castable material.

Once the graft assembly 24 is formed, a suture 34 is coupled to the assembly. The suture 34 and prosthetic assembly 24 are threaded into the tunnel formed in the bone or bones, so as to position the prosthetics 20 and 20' near an opening of the tibial and femoral tunnel. A fastener 100 is engagably driven between the implants 50 and the internal surface 94 of the bore 96 formed in the tibia. This locks the graft assembly 24 to the bone. Appropriate tension is applied to the graft, which is fixed at its second end by a soft tissue/bone engaging fastener 100 or other suitable means.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A method for surgically coupling a soft tissue replacement into a tunnel of a bone comprising:
    forming a first loop in the soft tissue replacement, the first loop including a first portion, a second portion that is generally parallel to the first portion, and an end portion that connects the first portion to the second portion;
    coupling a first prosthetic having first and second ends over both of the first portion and the second portion of the first loop, the end portion of the first loop extending from the first end of the first prosthetic, and each of the first and the second portions of the first loop extending from the second end of the first prosthetic;
    forming a tunnel in a bone;
    determining an appropriate soft tissue replacement length;
    placing a portion of the first prosthetic within the tunnel; and
    fixing the relative position of the first prosthetic with respect to the tunnel;
    wherein coupling the first prosthetic to the first loop in the soft tissue replacement comprises positioning the first loop in the soft tissue replacement in a mold, and injecting a biocompatible polymer into the mold to form the first prosthetic over the first portion and the second portion of the first loop.

2. The method according to claim 1, further comprising:
    forming a second loop in the soft tissue replacement, the first loop and the second loop are at opposite ends of the soft tissue, the second loop is overall substantially similar to the first loop; and
    coupling a second prosthetic over the second loop, the second prosthetic is overall substantially similar to the first prosthetic.

3. The method according to claim 1, further comprising positioning a tying mechanism about the first loop in the soft tissue replacement so as to fix adjacent portions of the soft tissue replacement together.

4. The method according to claim 3, further comprising expanding the tying mechanism and inserting the first loop in the soft tissue replacement into the tying mechanism.

5. The method according to claim 4, wherein positioning the tying mechanism about the first loop in the soft tissue replacement is disposing a coil spring about the first loop in the soft tissue replacement.

6. A method of surgically coupling a soft tissue implant to a bone comprising:
    forming a first loop in the soft tissue replacement, the first loop including a first portion, a second portion that is generally parallel to the first portion, and an end portion;
    coupling a first prosthetic to the first portion and the second portion of the first loop to form a prosthetic assembly by positioning the first and second portions of the first loop within a mold and injecting a material into the mold, said first prosthetic positioned on the first loop such that an aperture is defined between a side of the first prosthetic and the end portion of the first loop;
    coupling a suture to the first loop by threading the suture through the aperture;
    forming a bore in a bone;
    passing the suture through the bore to position the first prosthetic within the bone; and
    fixing the relative position of the prosthetic with respect to the bone.

7. The method according to claim 6, further comprising positioning a second loop of soft tissue replacement within a mold and injecting a polymer into the mold to form a second prosthetic assembly.

8. The method according to claim 7, wherein injecting a polymer is injecting a resorbable polymer.

9. The method according to claim 6, wherein fixing the relative position of the prosthetic assembly with respect to the bone is positioning a fastener between the prosthetic and the bone.

10. The method of claim 6, wherein the mold further defines an exterior locking surface formed on the first prosthetic.

11. The method of claim 6, further comprising disposing a tying mechanism about the first loop to couple the first portion of the first loop to the second portion of the first loop, the tying mechanism is molded over to secure the tying mechanism to the first loop.

12. The method of claim 6, wherein the first prosthetic is positioned on the first loop such that the end portion of the first loop is spaced apart from the side of the first prosthetic.

13. A method of coupling a soft tissue replacement to a bone comprising:

disposing a tying mechanism about a loop of soft tissue replacement material so as to constrict portions of the loop of soft tissue replacement material together;

molding a first prosthetic having a textured exterior surface, and first and second prosthetic ends around a first end of the loop of soft tissue replacement material to form a prosthetic assembly, a portion of said loop of soft tissue replacement protruding from the first and second prosthetic ends, the first prosthetic is molded over the tying mechanism;

measuring an anatomical distance;

intra-operatively coupling a second prosthetic to a second end of the loop of soft tissue replacement material so that the length of the prosthetic assembly is a function of the measured anatomical distance; and passing the prosthetic assembly through a tunnel in the bone to position the prosthetic assembly within the tunnel.

14. The method according to claim 13 further including forming a threaded surface onto an outer surface of the first prosthetic.

* * * * *